(12) United States Patent
Bergbauer et al.

(10) Patent No.: US 8,088,807 B2
(45) Date of Patent: Jan. 3, 2012

(54) MICROBICIDAL COMPOSITION

(75) Inventors: Mary Jo Bergbauer, Merchantville, NJ (US); John Vincent Berrier, Bordentown, NJ (US); Richard Walter Nichols, Langhorne, PA (US)

(73) Assignee: Rohm and Haas Company, Philadelphia, PA (US)

( * ) Notice: Subject to any disclaimer, the term of this patent is extended or adjusted under 35 U.S.C. 154(b) by 1206 days.

(21) Appl. No.: 11/807,403

(22) Filed: May 29, 2007

(65) Prior Publication Data

US 2007/0281043 A1    Dec. 6, 2007

Related U.S. Application Data

(60) Provisional application No. 60/857,877, filed on Nov. 10, 2006, provisional application No. 60/810,584, filed on Jun. 2, 2006.

(51) Int. Cl.
| | |
|---|---|
| *A01N 43/80* | (2006.01) |
| *A01N 25/00* | (2006.01) |
| *A01N 59/08* | (2006.01) |
| *A01N 59/00* | (2006.01) |
| *A61K 31/425* | (2006.01) |
| *A61K 9/00* | (2006.01) |
| *A61K 8/02* | (2006.01) |
| *A61K 33/14* | (2006.01) |
| *A61K 33/00* | (2006.01) |

(52) U.S. Cl. ........ 514/372; 424/400; 424/401; 424/405; 424/681; 424/718

(58) Field of Classification Search .................. None
See application file for complete search history.

(56) References Cited

U.S. PATENT DOCUMENTS

| | | | |
|---|---|---|---|
| 3,870,795 A | 3/1975 | Miller et al. | |
| 4,067,878 A | 1/1978 | Miller et al. | |
| 4,105,431 A | 8/1978 | Lewis et al. | |
| 4,241,214 A | 12/1980 | Miller et al. | |
| 4,310,590 A | 1/1982 | Petigara | |
| 4,396,413 A | 8/1983 | Miller et al. | |
| 4,939,266 A | 7/1990 | Bayer et al. | |
| 5,068,338 A | 11/1991 | Bayer et al. | |
| 5,312,827 A | 5/1994 | Bayer et al. | |
| 5,317,899 A | 6/1994 | Hutchinson et al. | |
| 5,466,818 A | 11/1995 | Petigara | |
| 5,910,503 A | 6/1999 | Mattox et al. | |
| 2003/0004198 A1* | 1/2003 | Still et al. ............... | 514/372 |

FOREIGN PATENT DOCUMENTS

KR    2002/85471 A    11/2002

* cited by examiner

*Primary Examiner* — Yong Chong
*Assistant Examiner* — Jody Karol
(74) *Attorney, Agent, or Firm* — Kenneth Crimaldi

(57) ABSTRACT

A microbicidal composition comprising relatively high levels of a mixture of 5-chloro-2-methyl-4-isothiazolin-3-one and 2-methyl-4-isothiazolin-3-one; a metal nitrate; and water. The composition optionally contains magnesium chloride.

2 Claims, No Drawings

MICROBICIDAL COMPOSITION

This application claims the benefit of priority under 35 U.S.C. §119(e) of U.S. Provisional Patent Application No. 60/857,877 filed on Nov. 10, 2006 and U.S. Provisional Application Ser. No. 60/810,584 filed on Jun. 2, 2006.

This invention relates to stable microbicidal compositions containing relatively high levels of 5-chloro-2-methylisothiazolin-3-one and 2-methylisothiazolin-3-one.

A composition containing a mixture of 5-chloro-2-methylisothiazolin-3-one and 2-methylisothiazolin-3-one in a total amount of 25% by weight is disclosed in U.S. Pat. No. 5,910,503. The composition is stabilized by a metal nitrate and a metal iodate. However, there is a need for additional stabilized microbicides, especially those having higher concentrations of active ingredients and/or greater stability.

The problem addressed by this invention is to provide such additional stabilized microbicides.

STATEMENT OF THE INVENTION

The present invention is directed to a microbicidal composition comprising: (a) 25-40% of a mixture of 5-chloro-2-methyl-4-isothiazolin-3-one and 2-methyl-4-isothiazolin-3-one; (b) 5-30% of a metal nitrate; and (c) water.

The present invention is further directed to a method for producing a microbicidal composition comprising: (a) 18-35% of a mixture of 5-chloro-2-methyl-4-isothiazolin-3-one and 2-methyl-4-isothiazolin-3-one; (b) 5-30% of a metal nitrate; and (c) water. The method comprises steps of: (i) adding hydrochloride salts of 5-chloro-2-methyl-4-isothiazolin-3-one and 2-methyl-4-isothiazolin-3-one to a solution of the metal nitrate and water to form an aqueous mixture; and (ii) adding magnesium oxide to the aqueous mixture to neutralize the hydrochloride salts.

DETAILED DESCRIPTION OF THE INVENTION

"MI" is 2-methyl-4-isothiazolin-3-one, also referred to by the name 2-methyl-3-isothiazolone. "CMI" is 5-chloro-2-methyl-4-isothiazolin-3-one, also referred to by the name 5-chloro-2-methyl-3-isothiazolone. Preferably, the weight ratio of CMI to MI is at least 1:1, alternatively at least 2:1. Preferably, the weight ratio of CMI to MI is no greater than 4:1. In one preferred embodiment of the invention, the CMI: MI ratio is about 3:1.

As used herein, the following terms have the designated definitions, unless the context clearly indicates otherwise. The term "microbicide" refers to a compound capable of inhibiting the growth of or controlling the growth of microorganisms at a locus; microbicides include bactericides, fungicides and algaecides. The term "microorganism" includes, for example, fungi (such as yeast and mold), bacteria and algae. The term "locus" refers to an industrial system or product subject to contamination by microorganisms. The following abbreviations are used throughout the specification: ppm=parts per million by weight (weight/weight), mL=milliliter, AI=active ingredient, i.e., total amount of isothiazolones. Unless otherwise specified, temperatures are in degrees centigrade (° C.), and references to percentages (%) are by weight.

In one embodiment of the invention, the composition contains at least 26% of a mixture of CMI and MI, alternatively at least 27%, alternatively at least 28%, alternatively at least 29%, alternatively at least 30%. In one embodiment, the composition contains no more than 37% CMI/MI, alternatively no more than 36%, alternatively no more than 35%.

A "metal nitrate" preferably is a nitrate salt of an alkali metal, an alkaline earth metal, or ammonium. Preferably, the metal is lithium, sodium, potassium, magnesium, calcium, ammonium, or a combination thereof; more preferably sodium, potassium, magnesium, or combinations thereof. Magnesium is especially preferred. Preferably, the amount of metal nitrate is at least 7%, alternatively at least 10%, alternatively at least 12%, alternatively at least 15%. Preferably, the amount of metal nitrate is no more than 27%, alternatively no more than 25%, alternatively no more than 22%, alternatively no more than 20%, alternatively no more than 18%. For CMI/MI concentrations at least 27%, a preferred metal nitrate concentration is from 5% to 27%, alternatively from 7% to 27%, alternatively from 7% to 25%, alternatively from 10% to 22%. For CMI/MI concentrations at least 29%, a preferred metal nitrate concentration is from 5% to 25%, alternatively from 5% to 22%, alternatively from 7% to 22%, alternatively from 7% to 20%, alternatively from 7% to 18%.

In one embodiment of the invention, the microbicidal composition is prepared by adding an acidic salt of CMI/MI, preferably a hydrochloride salt, to a solution of the metal nitrate and then neutralizing the acidic salt with a basic oxide, or carbonate, e.g., magnesium oxide, basic magnesium carbonate ($4MgCO_3 \cdot Mg(OH)_2 \cdot 6H_2O$), sodium bicarbonate, sodium carbonate, potassium bicarbonate, potassium carbonate, calcium oxide and calcium carbonate. Magnesium oxide is especially preferred. Addition of metal nitrate prior to neutralization is a suitable method for producing aqueous CMI/MI compositions over a broad range of concentrations, even those outside the scope of the present invention. In this embodiment of the invention, the composition which is prepared contains 18-35% of a mixture of CMI/MI. Preferably, the composition contains no more than 33% of a mixture of CMI/MI, alternatively no more than 32%, alternatively no more than 30%. Preferably, the composition contains at least 20% of a mixture of CMI/MI, alternatively at least 22%, alternatively at least 24%.

In another embodiment of the invention, the microbicidal composition is prepared by combining the free base forms of CMI and MI (available as Technical Grade CMI/MI) with a metal nitrate. In this embodiment, preferably the metal nitrate content of the composition is at least 15%, alternatively at least 18%, alternatively at least 19%, alternatively at least 20%. This method is especially suitable for preparing higher concentrations of CMI/MI, e.g., 32-40%.

In one embodiment, the composition further comprises 6% to 13% magnesium chloride, sodium chloride, potassium chloride or calcium chloride; alternatively 9% to 12%. The chloride salts may be added or generated by neutralization of CMI/MI hydrochlorides. Magnesium chloride is especially preferred.

In one embodiment, the composition further comprises a copper salt as a stabilizer. Preferred copper salts are copper nitrate and copper sulfate, in amounts from 1 to 200 ppm of copper.

In one embodiment of the invention, the composition comprises 30% to 60% water. Preferably, the amount of water is no more than 55%, alternatively no more than 50%, alternatively no more than 45%. Preferably, the amount of water is at least 35%, alternatively at least 38%.

In one embodiment of the invention, the composition is substantially free of bromic acid, iodic acid, periodic acid or their salts, i.e., the composition contains less than 0.01% of these substances, alternatively less than 0.005%, alternatively less than 0.001%.

The microbicidal compositions of the present invention can be used to inhibit the growth of microorganisms or higher forms of aquatic life (such as protozoans, invertebrates, bryozoans, dinoflagellates, crustaceans, mollusks, etc) by introducing a microbicidally effective amount of the compositions onto, into, or at a locus subject to microbial attack. Suitable loci include, for example: industrial process water; electrocoat deposition systems; cooling towers; air washers; gas scrubbers; mineral slurries; wastewater treatment; ornamental fountains; reverse osmosis filtration; ultrafiltration; ballast water; evaporative condensers; heat exchangers; pulp and paper processing fluids and additives; starch; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners; cosmetics; toiletries; shampoos; soaps; detergents; industrial cleaners; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; food, beverage, and industrial process pasteurizers; toilet bowls; recreational water; pools; and spas.

EXAMPLES

Example 1

Preparation of 30% Aqueous CMI/MI Solution From the Hydrochloride Salt

Into a 100 mL jacketed kettle equipped with a magnetic spinbar, pH probe, thermocouple, screw-feed addition funnel and water-cooled condenser, was placed 46.3 g of 40% aqueous magnesium nitrate, 7.3 g water and the hydrochloride salt of a CMI/MI mixture (35 g, 0.197 mol). The slurry was neutralized to pH 2.0 with magnesium oxide, keeping the temperature between 25°-30° C.

The neutralized solution was heat treated at 60° C. for 3 hours, cooled and filtered to give 87.1 g of product.

Storage Stability

Samples prepared by the method described above were divided into 0.5 oz (15 mL) vials and stored at 55° C. for 4 weeks. Samples were taken at 4 weeks and analyzed for % of the original CMI/MI remaining (AI rem.). Results are tabulated below, along with initial CMI/MI content of the formulation (% $AI_i$), % $Mg(NO_3)_2$ (% MN), % $MgCl_2$ in the formulation based on MgO used (% MC), % water determined by difference.

| % $AI_i$ | % MN | % MC | % $H_2O$ | AI rem. |
|---|---|---|---|---|
| 34.91 | 18.05 | 11.64 | 35.40 | 98.3 |
| 34.65 | 15.73 | 11.64 | 38.01 | 99.7 |
| 34.79 | 10.29 | 11.64 | 43.27 | 100 |
| 30.49 | 25.46 | 9.97 | 34.04 | 100 |
| 29.56 | 21.33 | 9.97 | 39.17 | 99.2 |
| 29.52 | 20.03 | 10.35 | 40.13 | 100[a] |
| 30.69 | 12.02 | 10.00 | 47.28 | 96.8 |
| 26.83 | 23.3 | 10.00 | 39.87 | 100[a] |
| 26.42 | 15.05 | 9.46 | 49.02 | 100[a] |
| 25.23 | 24.47 | 8.44 | 41.83 | 100[a] |
| 24.80 | 20.57 | 8.53 | 46.07 | 100[a] |
| 25.25 | 15.03 | 8.50 | 51.25 | 100[a] |
| 20.23 | 24.48 | 6.72 | 48.55 | 97.8 |
| 20.62 | 20.52 | 6.83 | 53.26 | 100[a] |
| 20.24 | 15.16 | 6.72 | 57.84 | 100[a] |

[a] results were > 100%

All samples were clear, yellow and free of solids. Further results are tabulated below.

| % $AI_i$ | % MN | % MC | % $H_2O$ | AI rem. |
|---|---|---|---|---|
| 31.01 | 17.0 | 10.16 | 41.82 | 98.5 |
| 30.25 | 21.9 | 10.16 | 37.72 | 99.4 |
| 30.91 | 12.1 | 10.16 | 46.85 | 97.7 |
| 29.64 | 6.5 | 10.16 | 53.66 | 84.9 |
| 25.01 | 21.5 | 8.49 | 44.98 | 98.9 |
| 24.60 | 16.8 | 8.49 | 50.08 | 100 |
| 26.34 | 11.7 | 8.49 | 53.49 | 96.3 |
| 24.84 | 6.4 | 8.49 | 60.25 | 5.9 |

Example 2

Preparation of Aqueous CMI/MI Solution from Technical Grade CMI/MI

Into a 100 mL jacketed kettle equipped with a magnetic spinbar and thermocouple was placed 50.0 g of 40% aqueous magnesium nitrate, 20.0 g of water and 30.0 g of Technical grade CMI/MI. The mixture was stirred at 25°-30° C. until all of the CMI/MI dissolved. The solution was heat treated at 60° C. for 3 hours, cooled and filtered to give 97.5 g of product. In some samples, magnesium chloride was added as a 30% aqueous solution. Results are presented below for samples stored for 4 weeks at 55° C. Higher % MN is required for samples prepared by this method, especially at higher % $H_2O$.

| % $AI_i$ | % MN | % MC | % $H_2O$ | AI rem. |
|---|---|---|---|---|
| 39.60 | 19.1 | 0 | 41.30 | 94.8 |
| 35.07 | 24.1 | 0 | 40.83 | 100.0 |
| 36.08 | 20.0 | 0 | 43.92 | 94.7 |
| 34.79 | 10.2 | 0 | 55.01 | 5.7 |
| 29.80 | 19.5 | 0 | 50.70 | 90.1 |
| 29.75 | 10.3 | 0 | 59.95 | 4.8 |
| 14.62 | 19.6 | 0 | 65.78 | 94.3 |
| 32.87 | 25.7 | 0 | 41.39 | 96.1 |
| 31.91 | 20.7 | 0 | 47.44 | 96.5 |
| 32.50 | 20.9 | 10.00 | 36.59 | 99.3 |
| 32.03 | 16.0 | 0 | 51.96 | 26.1 |
| 31.86 | 15.8 | 10.00 | 42.37 | 100.0 |
| 31.91 | 11.0 | 0 | 57.07 | 0.0 |
| 32.14 | 11.3 | 10.00 | 46.57 | 98.0 |
| 27.78 | 18.1 | 0 | 54.16 | 96.2 |
| 14.92 | 19.4 | 6.00 | 59.72 | 98.9 |

Comparative Example 1

Preparation of High-Concentration CMI/MI by Addition of Magnesium Nitrate After Neutralization If the hydrochloride of CMI/MI is neutralized with magnesium oxide, and magnesium nitrate hexahydrate is added only after neutralization ("MN 6H₂O after") or 40% magnesium nitrate is added only after neutralization ("40% MN after"), the following solids contents are required before neutralization to achieve the indicated high concentrations. They are tabulated below for products with different % AI and % MN contents, with the % solids contents required with pre-addition of 40% MN, as in Ex. 1 ("MN before"). Mixtures with solids content above about 45% cannot be agitated well. Production of mixtures having high AI content by post-addition of MN is not feasible. In all cases, the solids content before neutralization is lower for pre-addition of 40% MN.

| % AI | % MN | minimum % solids for "40% MN after" | minimum % solids for "MN 6H$_2$O after" | minimum % solids for "MN before" |
|---|---|---|---|---|
| 35 | 25 | NA[1] | 85 | 46 |
| 35 | 20 | 98 | 73 | 46 |
| 35 | 15 | 76 | 64 | 46 |
| 30 | 25 | NA[1] | 72 | 39 |
| 30 | 20 | 83 | 62 | 39 |
| 30 | 15 | 65 | 54 | 39 |
| 25 | 25 | 93 | 59 | 33 |
| 25 | 20 | 68 | 51 | 33 |
| 25 | 15 | 53 | 45 | 33 |
| 20 | 25 | 73 | 47 | 26 |
| 20 | 20 | 53 | 40 | 26 |
| 20 | 15 | 42 | 35 | 26 |

[1]It is not possible to prepare these AI/MN compositions with post-addition of 40% MN

The invention claimed is:

1. A microbicidal composition comprising:
   (a) 27-37% of a mixture of 5-chloro-2-methyl-4-isothiazolin-3-one and 2-methyl-4-isothiazolin-3-one in which the weight ratio of 5-chloro-2-methyl-4-isothiazolin-3-one to 2-methyl-4-isothiazolin-3-one is from 4:1 to 1:1;
   (b) 12-27% of a metal nitrate;
   (c) 35-50% water; and
   (d) 9-12% magnesium chloride;
   wherein the composition is substantially free of bromic acid, iodic acid, periodic acid or their salts.

2. The composition of claim 1 having 27-35% of a mixture of 5-chloro-2-methyl-4-isothiazolin-3-one and 2-methyl-4-isothiazolin-3-one, 38-50% water and 15-22% of a metal nitrate.

* * * * *